(12) United States Patent
Chen et al.

(10) Patent No.: US 8,173,822 B2
(45) Date of Patent: May 8, 2012

(54) 1,3-OXATHIANE COMPOUNDS AND THEIR USE IN FLAVOR AND FRAGRANCE COMPOSITIONS

(75) Inventors: Zhen Chen, Aberdeen, NJ (US); Mark L. Dewis, Matawan, NJ (US); Debra Merritt, Hopewell, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 541 days.

(21) Appl. No.: 12/261,538

(22) Filed: Oct. 30, 2008

(65) Prior Publication Data

US 2010/0111880 A1    May 6, 2010

(51) Int. Cl.
C07D 327/06 (2006.01)
A61K 31/39 (2006.01)
A61K 8/49 (2006.01)
A23L 2/56 (2006.01)
(52) U.S. Cl. ............. 549/14; 514/433; 424/49; 426/535
(58) Field of Classification Search ....................... 549/13
See application file for complete search history.

(56) References Cited

U.S. PATENT DOCUMENTS

| 4,220,561 A | 9/1980 | Winter et al. |
| 4,364,400 A | 12/1982 | Winter et al. |
| 6,559,109 B2 | 5/2003 | Lelandais |

*Primary Examiner* — Andrew D Kosar
*Assistant Examiner* — Karen Cheng
(74) *Attorney, Agent, or Firm* — Elizabeth M. Quirk; XuFan Tsang; Joseph F. Leightner

(57) ABSTRACT

The present invention relates to novel 1,3-oxathiane compounds represented by Formula I:

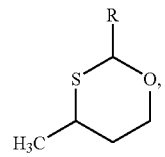

Formula I wherein R is selected from the group consisting of ethyl, butyl, propyl, and (methylthio)ethyl, and their uses to enhance a flavor or fragrance composition.

4 Claims, No Drawings

1,3-OXATHIANE COMPOUNDS AND THEIR USE IN FLAVOR AND FRAGRANCE COMPOSITIONS

FIELD OF THE INVENTION

The present invention relates to new chemical entities and the incorporation and use of the new chemical entities as flavor and fragrance materials.

BACKGROUND OF THE INVENTION

There is an ongoing need in the fragrance industry to provide new chemicals to give perfumers and other persons the ability to create new fragrances for perfumes, colognes and personal care products. There is a similar ongoing need for flavor chemicals that enhance or provide new flavors for food preparations. Those with skill in the art appreciate how differences in the chemical structures of the molecules can result in significant differences in the odor, notes and characteristics. The identification of structural variations and discovery of new chemicals enable the creation of new flavors and fragrances.

SUMMARY OF THE INVENTION

The present invention provides novel chemicals, and their use to enhance the fragrance of perfumes, toilet waters, colognes, personal products and the like. In addition, the present invention is directed to the use of novel chemicals to enhance the flavor of beverages, foodstuff, chewing gums, dental and oral hygiene products and the like.

More specifically, the present invention is directed to 1,3-oxathiane compounds and a method of improving, enhancing or modifying a fragrance or a flavor formulation through the addition of an olfactory acceptable amount of 1,3-oxathiane compounds represented by Formula I set forth below:

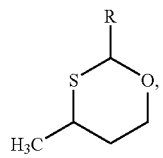

Formula I wherein R is selected from the group consisting of ethyl, butyl, propyl, and 2-(methylthio)ethyl.

Another embodiment of the invention is directed to a composition comprising the 1,3-oxathiane compounds provided above and a material selected from the group consisting of a foodstuff, a chewing gum, a medicinal product, toothpaste, a perfumery product, and a perfume cleaning agent.

Another embodiment of the invention is directed to a process of augmenting, enhancing or imparting taste to a material by incorporating an olfactory acceptable amount of the 1,3-oxathiane compounds provided above.

Another embodiment of the invention is directed to a method of improving, enhancing or modifying a fragrance formulation by incorporating an olfactory acceptable amount of the 1,3-oxathiane compounds provided above.

These and other embodiments of the present invention will be apparent by reading the following specification.

DETAILED DESCRIPTION OF THE INVENTION

It is known to those with the skill in the art that Formula I as defined above provides the following novel compounds:

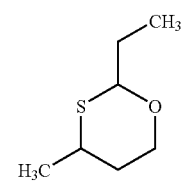

Formula II

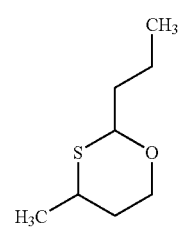

Formula III

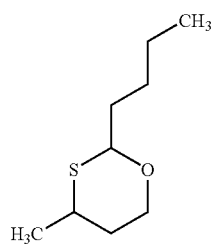

Formula IV

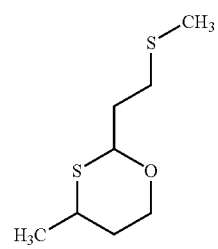

Formula V

Those with the skill in the art will recognize that

Formula II represents 2-ethyl-4-methyl-1,3-oxathiane;

Formula III represents 2-propyl-4-methyl-1,3-oxathiane;

Formula IV represents 2-butyl-4-methyl-1,3-oxathiane; and

Formula V represents 4-methyl-2-[2-(methylthio)ethyl]-1,3-oxathiane.

The compounds of the present invention may be prepared via a cyclization reaction of 3-mercapto-1-butanol with aldehydes. The preparation of 3-mercapto-1-butanol is illustrated below in Example I. Those with the skill in the art will appreciate that suitable aldehydes include, for example, propionaldehyde, butyraldehyde, valeraldehyde, and 3-methylthio-propionaldehyde.

The cyclization reaction can be depicted by a general scheme as follows:

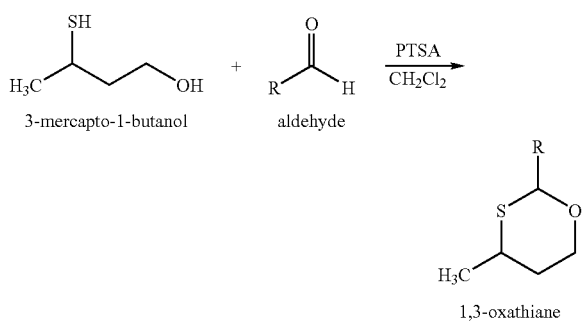

wherein R is defined as above;
PTSA represents paratoluenesulfonic acid monohydrate; and
$CH_2Cl_2$ represents dichloromethane.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The compounds of the present invention are found to have unexpected strong and long-lasting organoleptic properties, which are shown to be advantageous for their use in augmenting or imparting taste enhancement or somatosensory effect to foodstuffs, chewing gums, medicinal products, and toothpaste by providing flavor enhancement and a preferred overall flavor profile.

The present invention further relates to a process of augmenting or imparting taste or somatosensory effect to foodstuffs, chewing gums, medicinal products, and toothpaste by adding the compounds of the present invention.

The use of the compounds of the present invention is also widely applicable in current perfumery products, including perfumes, colognes, personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

When used in a fragrance formulation, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

As used herein, an olfactory effective amount is understood to mean the amount of the compound in a flavor or fragrance composition contributes to its particular olfactory characteristics, but the flavor, taste and aroma effect on the overall composition will be the sum of the effect of each flavor or fragrance ingredient. Thus the compounds of the present invention can be used to alter the characteristics of a flavor or fragrance composition, or by modifying the flavor, taste and aroma reaction contributed by another ingredient in the composition. The amount will vary depending on many factors including other ingredients, their relative amounts and the effect that is desired.

The usage level of the 1,3-oxathiane compounds varies depending on the product in which the compounds are employed. Generally, the level of the 1,3-oxathiane compounds employed in a product is greater than about 0.1 parts per billion by weight, preferably from about 0.1 to about 500 parts per billion by weight, more preferably from about 0.5 to about 100 parts per billion by weight.

The term "foodstuff" as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the 1,3-oxathiane compounds of the present invention are used in a flavoring composition, they can be combined with conventional flavoring materials or adjuvants, which are well known in the art and have been extensively described in the past. Conventional flavoring materials include saturated fatty acids, unsaturated fatty acids, amino acids; alcohols including primary and secondary alcohols; esters; carbonyl compounds including ketones; aldehydes; lactones; cyclic organic materials including benzene derivatives, acyclic compounds, heterocyclies such as furans, pyridines, pyrazines and the like; sulfur-containing compounds including thiols, sulfides, disulfides and the like; proteins; lipids; carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like; and artificial flavoring materials such as vanillin, ethyl vanillin and the like. Requirements for adjuvants include: (1) that they be non-reactive with the 1,3-oxathiane compounds of the present invention; (2) that they be organoleptically compatible with the 1,3-oxathiane compounds of the present invention, whereby the flavor of the ultimate consumable product to which the 1,3-oxathiane compounds are added is not detrimentally affected by the use of the adjuvants; and (3) that they be ingestible acceptable and thus nontoxic or otherwise non-deleterious.

In addition, other flavor materials, vehicles, stabilizers, thickeners, surface active agents, conditioners and flavor intensifiers can also be included.

The following are provided as specific embodiments of the present invention. Other modifications of this invention will be readily apparent to those skilled in the art. Such modifications are understood to be within the scope of this invention. As used herein all percentages are weight percent unless otherwise noted, ppb is understood to stand for parts per billion, ppm is understood to stand for parts per million, L is understood to be liter, mL is understood to be milliliter, Kg is understood to be kilogram, g is understood to be gram, mol is understood to be mole, and mmHg be millimeters (mm) of mercury (Hg). IFF as used in the examples is understood to mean International Flavors & Fragrances Inc., New York, N.Y., USA.

EXAMPLE I

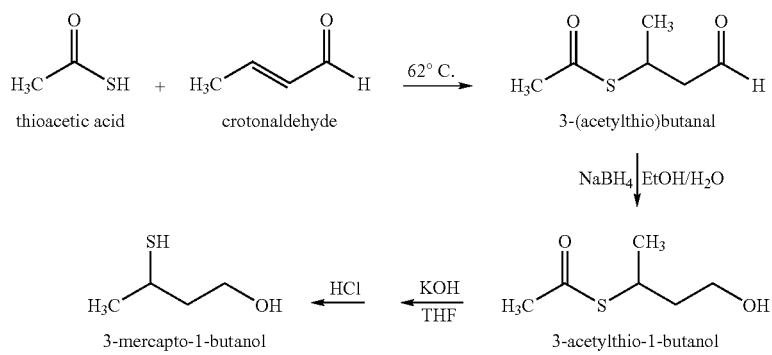

Preparation of 3-Mercapto-1-butanol: Thioacetic acid (385 mL, 5.4 mol, commercially available from Sigma-Aldrich, Inc., Inc.) and crotonaldehyde (440 mL, 5.4 mol, commercially available from Acros Organics) were used to provide 3-(acetylthio)butanal (640 g), which was treated with sodium borohydride ($NaBH_4$, commercially available from Acros Organics) to provide 3-acetylthio-1-butanol, which was consequently hydrolyzed, and distilled under vacuum to provide the product of 3-mercapto-1-butanol (165 g), which had boiling points of 90° C. at a pressure of 29 mmHg, and 85° C. at 18 mmHg.

EXAMPLE II

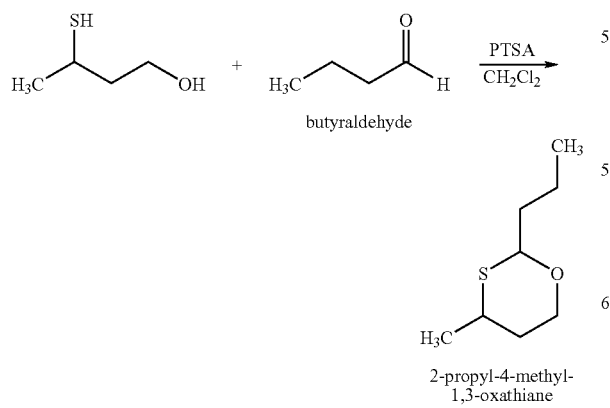

Preparation of 2-Propyl-4-methyl-1,3-oxathiane (Formula III): A solution of 3-mercapto-1-butanol (106 g, 1 mol, synthesized as above) and PTSA (paratoluenesulfonic acid monohydrate, 38 g, 0.2 mol, commercially available from Sigma-Aldrich, Inc.) in 400 mL of $CH_2Cl_2$ (dichloromethane) were cooled with an ice bath. Butyraldehyde (106 mL, 1,2 mol, commercially available from Sigma-Aldrich, Inc.) was added drop wise to the solution, and the reaction mixture was stirred with cooling for half an hour and at room temperature for another 1 hour. The reaction mixture was washed twice with saturated sodium bicarbonate solution and once with brine. The organic phase was then dried with anhydrous magnesium sulfate. The solvent was removed with a rotary evaporator and the crude product was distilled under vacuum to provide 2-ethyl-4-methyl-1,3-oxathiane (98 g), which had a boiling point of 80° C. at a pressure of 10.4 mmHg.

$^1$H NMR ($CDCl_3$) δ: 0.93 (t, 3H, J=7.38 Hz), 1.22 (d, ~85% of 3H, J=6.75 Hz), 1.34-1.83 (m, 6H, +~15% of 3H), 3.04-3.19 (m, 1H), 3.54 (t, ~85% of 1H, J=12.23 Hz, of d, J=2.09 Hz), 3.86 (t, ~15% of 1H, J=11.90 Hz, of d, J=2.24 Hz), 3.94 (d, ~15% of 1H, J=12.14 Hz, of t, J=3.98 Hz), 4.19 (d, ~85% of 1H, J=11.95 Hz, of d, J=4.00 Hz, of d, J=2.21 Hz), 4.69 (d, ~85% of 1H, J=6.74 Hz, of d, J=5.59 Hz), 4.94 (d, ~15% of 1H, J=7.07 Hz, of d, J=5.49 Hz).

EXAMPLE III

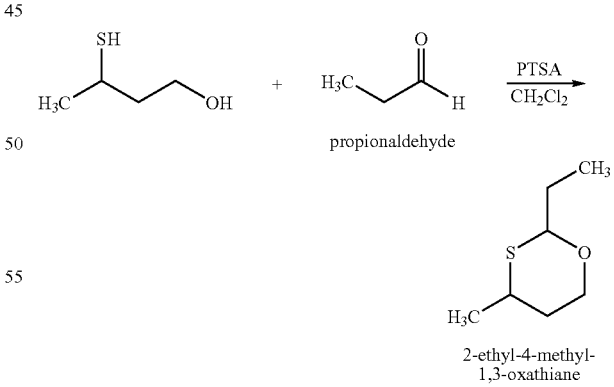

Preparation of 2-Ethyl-4-methyl-1,3-oxathiane (Formula II): 2-Ethyl-4-methyl-1,3-oxathiane was prepared according to the same scheme of Example II. 2-Ethyl-4-methyl-1,3-oxathiane (14.1 g) was produced with 3-mercapto-1-butanol (15.9 g) and propionaldehyde (8.7 g, commercially available from Sigma-Aldrich, Inc.). The product had a boiling point of 82° C. at a pressure of 20 mmHg.

$^1$H NMR (CDCl$_3$) δ: 1.00 (t, 3H, J=7.49 Hz), 1.23 (d, ~84% of 3H, J=6.74 Hz), 1.47-1.64 (d, ~16% of 3H, J=7.19 Hz, +1H), 1.65-1.75 (m, 1H, +~84% of 1H), 1.76-1.86 (m, 1H), 2.17-2.24 (m, ~16% of 1H), 3.04-3.11 (m, ~84% of 1H), 3.14-3.18 (m, ~16% of 1H), 3.54 (t, ~84% of 1H, J=12.22 Hz), 3.87 (t, ~16% of 1H, J=11.85 Hz), 3.93-3.98 (m, ~16% of 1H), 4.18-4.21 (m, ~84% of 1H), 4.63 (t, ~84% of 1H, J=6.08), 4.86 (t, ~16% of 1H, J=6.20).

EXAMPLE IV

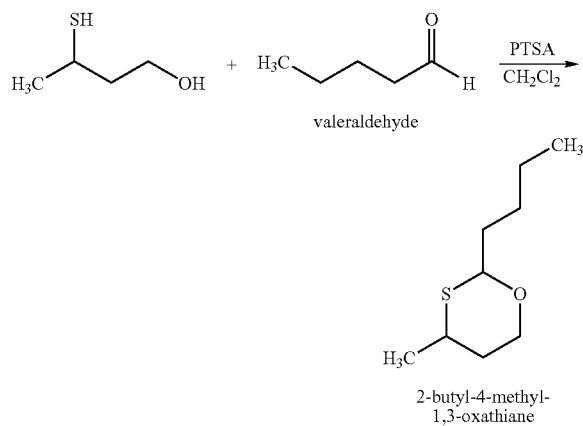

2-butyl-4-methyl-1,3-oxathiane

Preparation of 2-Butyl-4-methyl-1,3-oxathiane (Formula IV): 2-Butyl-4-methyl-1,3-oxathiane was prepared according to the same scheme of Example II. 2-Butyl-4-methyl-1,3-oxathiane (20.0 g) was produced with 3-mercapto-1-butanol (21.2 g) and valeraldehyde (17.2 g, commercially available from Acros Organics). The product had a boiling point of 95° C. at a pressure of 7.8 mmHg.

$^1$H NMR (CDCl$_3$) δ: 0.90 (t, 3H, J=7.22 Hz), 1.22 (d, ~87% of 3H, J=6.74 Hz), 1.29-1.83 (m, 8H, +~13% of 3H), 3.04-3.12 (m, ~87% of 1H), 3.13-3.19 (m, ~13% of 1H), 3.54 (t, ~87% of 1H, J=12.20 Hz, of d, J=1.76 Hz), 3.86 (t, ~13% of 1H, J=11.87 Hz, of d, J=1.86 Hz), 3.94 (d, ~13% of 1H, J=12.16 Hz, of t, J=3.91 Hz), 4.18 (d, ~87% of 1H, J=11.93 Hz, of m), 4.68 (t, ~87% of 1H, J=6.14 Hz), 4.92 (t, ~13% of 1H, J=6.27).

EXAMPLE V

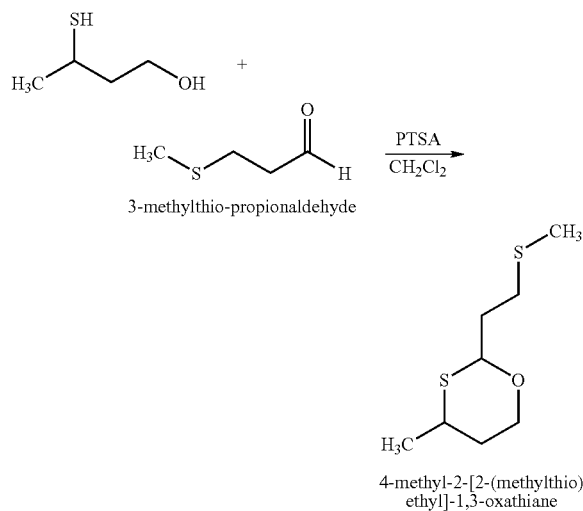

4-methyl-2-[2-(methylthio)ethyl]-1,3-oxathiane

Preparation of 4-Methyl-2-[2-(methylthio)ethyl]-1,3-oxathiane (Formula V): 4-Methyl-2-[2-(methylthio)ethyl]-1,3-oxathiane was prepared according to the same scheme of Example II. 4-Methyl-2-[2-(methylthio)ethyl]-1,3-oxathiane (16.0 g) was produced with 3-mercapto-1-butanol (15.9 g) and 3-methylthio-propionaldehyde (15.4 g, commercially available from Sigma-Aldrich, Inc.). The product had a boiling point of 82° C. at a pressure of 0.6 mmHg.

$^1$H NMR (CDCl3) δ: 1.23 (d, ~86% of 3H, J=6.74 Hz), 1.48-1.57 (d, ~14% of 3H, J=7.21 Hz, and ~14% of 2H), 1.58-1.64 (m, ~86% of 1H), 1.71-1.75 (m, ~86% of 1H), 1.89-1.99 (m, 1H), 2.03-2.14 (m, ~86% of 1H), 2.10 (s, 3H), 2.16-2.24 (m, ~14% of 1H), 2.64 (t, 2H, J=7.38 Hz), 3.07-3.19 (m, 1H), 3.55 (t, ~86% of 1H, J=12.23 Hz, of d, J=1.55 Hz), 3.87 (t, ~14% of 1H, J=11.85 Hz, of d, J=2.01 Hz), 3.92-3.97 (m, ~14% of 1H), 4.17-4.21 (m, ~86% of 1H), 4.84 (d, ~86% of 1H, J=7.03 Hz, of d, J=5.09 Hz), 5.08 (d, ~14% of 1H, J=7.37 Hz, of d, J=5.03 Hz).

EXAMPLE VI

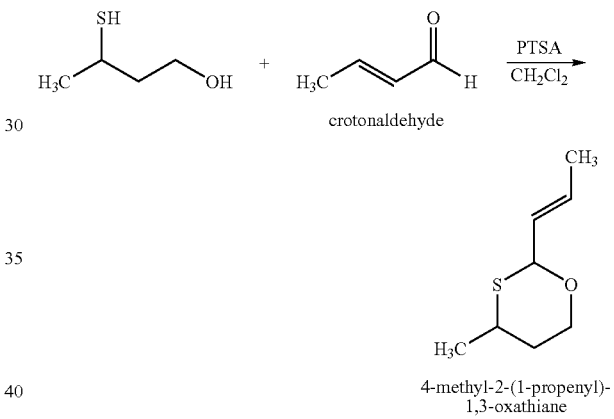

4-methyl-2-(1-propenyl)-1,3-oxathiane

Preparation of 4-Methyl-2-(1-propenyl)-1,3-oxathiane: 4-Methyl-2-(1-propenyl)-1,3-oxathiane was prepared according to the same scheme of Example II. 4-Methyl-2-(1-propenyl)-1,3-oxathiane (8.0 g) was produced with 3-mercapto-1-butanol (10.6 g) and crotonaldehyde (8.4 g, commercially available from Acros Organics). The product had a boiling point of 82° C. at a pressure of 9.0 mmHg.

$^1$H NMR (CDCl$_3$) δ: 1.23 (d, 3H, J=6.74 Hz), 1.57-1.66 (m, 1H), 1.70-1.75 (m, 4H), 3.09-3.18 (m, 1H), 3.59 (t, 1H, J=12.18 Hz, of d, J=2.06 Hz), 4.23 (d, 1H, J=12.00 Hz, of d, J=3.98 Hz, of d, J=2.29 Hz), 5.17 (d, 1H, J=6.17 Hz), 5.55-5.61 (m, 1H), 5.89 (d, 1H, J=15.40 Hz, of q, J=6.58 Hz).

EXAMPLE VII

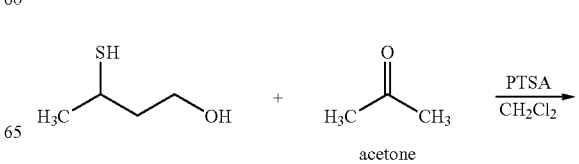

acetone

-continued

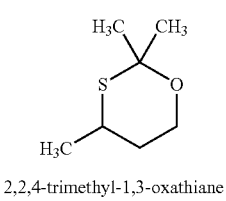

2,2,4-trimethyl-1,3-oxathiane

Preparation of 2,2,4-Trimethyl-1,3-oxathiane: 2,2,4-Trimethyl-1,3-oxathiane was prepared according to the same scheme of Example II. 2,2,4-Trimethyl-1,3-oxathiane (15.0 g) was produced with 3-mercapto-1-butanol (21.2 g) and acetone (11.6 g, commercially available from Sigma-Aldrich, Inc.). The product had a boiling point of 76° C. at a pressure of 21 mmHg.

$^1$H NMR (CDCl$_3$) δ: 1.19 (d, 3H, J=6.38 Hz), 1.48-1.58 (m, 1H), 1.53 (s, 3H), 1.68 (s, 3H), 1.71-1.75 (m, 1H), 3.16-3.21 (m, 1H), 3.85-3.95 (m, 2H).

EXAMPLE VIII

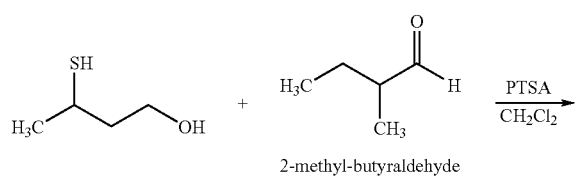

2-methyl-butyraldehyde

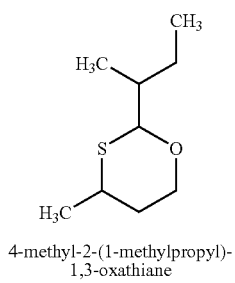

4-methyl-2-(1-methylpropyl)-1,3-oxathiane

Preparation of 4-Methyl-2-(1-methylpropyl)-1,3-oxathiane: 4-Methyl-2-(1-methylpropyl)-1,3-oxathiane was prepared according to the same scheme of Example II. 4-Methyl-2-(1-methylpropyl)-1,3-oxathiane (15.7 g) was produced with 3-mercapto-1-butanol (15.9 g) and 2-methyl-butyraldehyde (12.9 g, commercially available from Sigma-Aldrich, Inc.). The product had a boiling point of 90° C. at a pressure of 10.2 mmHg.

$^1$H NMR (CDCl$_3$) δ: 0.91 (t, 3H, J=7.43 Hz), 1.00 (d, 3H, J=10.2 Hz, of d, J=6.91 Hz(, 1.19-1.30 (d, ~15% of 3H), 1.24 (d, 3H, J=6.72 Hz), 1.45-1.80 (m, ~85% of 4H, and 1H), 2.18-2.26 (m, ~15% of 1H), 3.01-3.10 (m, ~85% of 1H), 3.14-3.22 (m, ~15% of 1H), 3.53 (t, ~85% of 1H, J=12.18 Hz), 3.86 (t, ~15% of 1H, J=12.01 Hz), 3.95 (d, ~15% of 1H, J=11.99 Hz, of t, J=3.73 Hz), 4.20 (d, ~85% of 1H, J=11.86 Hz, of m), 4.61 (d, ~85% of 1H, J=12.01 Hz, of d, J=5.08 Hz), 4.83 (d, ~15% of 1H, J=11.88 Hz, of d, J=5.61 Hz).

EXAMPLE IX

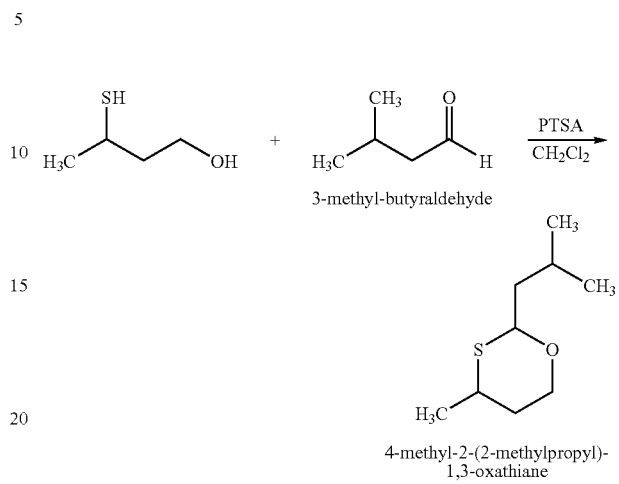

3-methyl-butyraldehyde 4-methyl-2-(2-methylpropyl)-1,3-oxathiane

Preparation of 4-Methyl-2-(2-methylpropyl)-1,3-oxathiane: 4-Methyl-2-(2-methylpropyl)-1,3-oxathiane was prepared according to the same scheme of Example II. 4-Methyl-2-(2-methylpropyl)-1,3-oxathiane (11.2 g) was produced using 3-mercapto-1-butanol (15.9 g) and 3-methyl-butyraldehyde (12.9 g, commercially available from Janssen Chimica). The product had a boiling point of 95° C. at a pressure of 11.1 mmHg.

$^1$H NMR (CDCl$_3$) δ: 0.91 (d, 3H, J=5.65 Hz), 0.92 (d, 3H, J=5.23 Hz), 1.22 (d, ~87% of 3H, J=6.73 Hz), 1.44-1.51 (m, 1H, +~13% of 1H), 1.54 (d, ~13% of 3H, J=7.19 Hz), 1.57-1.63 (m, ~87% of 1H), 1.66-1.79 (m, 1H, and ~87% of 1H), 1.80-1.91 (m, 1H), 2.17-2.27 (m, ~13% of 1H), 3.05-3.19 (m, 1H), 3.53 (t, ~87% of 1H, J=12.21 Hz), 3.86 (t, ~13% of 1H, J=11.92 Hz), 3.92-3.95 (m, ~13% of 1H), 4.18 (d, ~87% of 1H, J=11.10 Hz), 4.73 (d, ~87% of 1H, J=7.39 Hz, of d, J=5.53 Hz), 4.99 (d, ~13% of 1H, J=7.40 Hz, of d, J=5.56 Hz).

EXAMPLE X

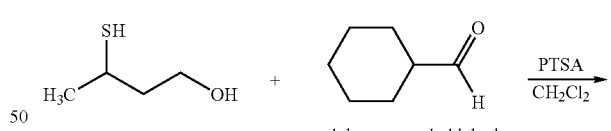

cyclohexanaecarbaldehyde

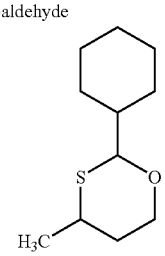

2-cyclohexyl-4-methyl-1,3-oxathiane

Preparation of 2-Cyclohexyl-4-methyl-1,3-oxathiane: 2-Cyclohexyl-4-methyl-1,3-oxathiane was prepared according to the same scheme of Example II. 2-Cyclohexyl-4-methyl-1,3-oxathiane (19.7 g) was produced using 3-mercapto- 1-butanol (15.9 g) and cyclohexanecarboxaldehyde (16.8 g, commercially available from Sigma-Aldrich, Inc.). The product had a boiling point of 85° C. at a pressure of 0.6 mmHg.

$^1$H NMR (CDCl$_3$) δ: 1.05-1.27 (m, 5H), 1.23 (d, ~83% of 3H, J=6.73 Hz), 1.45-1.81 (m, 6H, and ~83% of 1H), 1.52 (d, ~17% of 3H, J=7.19 Hz), 1.91 (d, 1H, J=12.16 Hz), 2.17-2.24 (m, ~17% of 1H), 3.00-3.08 (m, ~83% of 1H), 3.13-3.20 (m, ~17% of 1H), 3.51 (t, ~83% of 1H, J=12.36 Hz), 3.84 (t, ~17% of 1H, J=11.88 Hz), 3.94 (d, ~17% of 1H, J=12.15 Hz, of t, J=3.90 Hz), 4.19 (d, ~83% of 1H, J=11.92 Hz, of d, J=1.63 Hz), 4.53 (d, ~83% of 1H, of d, J=5.87 Hz), 4.73 (d, ~17% of 1H, of d, J=6.48 Hz).

EXAMPLE XI

The organoleptic properties of the above compounds (i.e., Examples II-X) were evaluated by a seven-member trained sensory panel using the intensity scale of 0 to 5, where 0=none, 1=weak, 2=moderate, 3=strong, 4=very strong, and 5=extremely strong. Averaged sensory scores were reported in the following:

| No. | Compound | Chemical Name | Odor Profile (0.5%) | Flavor Profile | Flavor Intensity |
|---|---|---|---|---|---|
| 1 | (structure) | 2-Propyl-4-methyl-1,3-oxathiane | Onion, garlic, powerful, sweet | Pineapple, milky, mango, grapey, citrus, bubblegum, melon, orange flower, cassis, alliaceous, bacon | 5 |
| 2 | (structure) | 2-Ethyl-4-methyl-1,3-oxathiane | Powerful, floral, fruity, apricot, dried papaya | Tropical, vegetable, green, waxy | 4 |
| 3 | (structure) | 2-Butyl-4-methyl-1,3-oxathiane | Powerful, green, spicy, leafy, woody, pepper, oily | Fruity, tropical, grapefruit, cantaloupe, banana | 4 |
| 4 | (structure) | 4-Methyl-2-[2-(methylthio)ethyl]-1,3-oxathiane | Powerful, garlic, animalic, onion, green, herbaceous | Potato, raw, vegetable | 4 |
| 5 | (structure) | 4-Methyl-2-(1-propenyl)-1,3-oxathiane | Garlic, green, starchy, pepper, balsamic, mossy, woody | Cabbage, sulfur | 2 |
| 6 | (structure) | 2,2,4-Trimethyl-1,3-oxathiane | Green, woody, terpenes, powerful | Fruity, tropical, green | 3 |

| No. | Compound | Chemical Name | Odor Profile (0.5%) | Flavor Profile | Flavor Intensity |
|---|---|---|---|---|---|
| 7 | (structure) | 4-Methyl-2-(1-methylpropyl)-1,3-oxathiane | Citrus, pamplemousse, grapefruit, lime, zesty | Vegetable, green, sulfury | 3 |
| 8 | (structure) | 4-Methyl-2-(2-methylpropyl)-1,3-oxathiane | Floral, woody, chemical, powerful | Fruity, berry, green, gooseberries | 1 |
| 9 | (structure) | 2-Cyclohexyl-4-methyl-1,3-oxathiane | Citrus, onion, herbaceous, dry wood | Slight tropical, slight onion | 1 |

Compound No.s. 1-4 (i.e., Formulas III, II, IV, and V) were demonstrated to have unexpected strong and long-lasting odors and flavors, superior to other 1,3-oxathiane compounds tested.

EXAMPLE XII

The Concord Grape flavor formulas were prepared as follows and tested at a level of 0.05%. 2-Propyl-4-methyl-1,3-oxathiane was demonstrated to impart juicy, flesh, and enhanced skin notes to the formula.

| Ingredients | Parts* + | Parts* − |
|---|---|---|
| Methyl anthranilate (Commercially available from Elan Chemical Company) | 5.00 | 5.00 |
| Furaneol (Commercially available from Lansdowne Chemical) | 1.00 | 1.00 |
| Cis-3-hexenol (Commercially available from Mitsui & Co., LTD) | 0.30 | 0.30 |
| Ethyl acetate (Commercially available from Symrise GMBH & Co.) | 0.80 | 0.80 |
| Phenyl ethyl alcohol (Commercially available from Advanced Biotech) | 0.10 | 0.10 |
| 2-Propyl-4-methyl-1,3-oxathiane, 1% | 0.002 | — |
| Propylene glycol (Commercially available from IFF) | 92.798 | 92.80 |
| Total | 100.00 | 100.00 |

*"+" represents a 2-propyl-4-methyl-1,3-oxathiane containing formula; and "−" represents a 2-propyl-4-methyl-1,3-oxathiane non-containing formula.

EXAMPLE XIII

The smoked bacon flavor formulas were prepared as follows and tested at a level of 0.02%. 2-Propyl-4-methyl-1,3-oxathiane was demonstrated to impart smoky, meaty, fatty, and enhanced crispy notes to the formula.

| Ingredients | Parts* + | Parts* − |
|---|---|---|
| Cyclotene (Commercially available from Polarome International, Inc.) | 6.5 | 6.5 |
| Pyridine (Commercially available from Sigma-Aldrich, Inc.) | 0.1 | 0.1 |
| Diacetyl (Commercially available from DSM Food Specialties B.V.) | 0.08 | 0.08 |
| Guaiacol (Commercially available from Advanced Biotech) | 0.12 | 0.12 |
| Isovaleric acid (Commercially available from Berje Inc.) | 0.05 | 0.05 |
| Acetic acid (Commercially available from Symrise GMBH & Co.) | 1.00 | 1.00 |
| Furfuryl mercaptan (Commercially available from Advanced Biotech) | 0.002 | 0.002 |
| Charoil Hickory (Commercially available from Red Arrow Products Co. LLC.) | 0.40 | 0.40 |
| 2-Propyl-4-methyl-1,3-oxathiane, 1% | 0.005 | — |
| Propylene glycol (Commercially available from IFF) | 91.743 | 91.748 |
| Total | 100.00 | 100.00 |

*"+" represents a 2-propyl-4-methyl-1,3-oxathiane containing formula; and "−" represents a 2-propyl-4-methyl-1,3-oxathiane non-containing formula.

EXAMPLE XIV

The guava flavor formulas were prepared as follows and tested at a level of 0.05%. 2-Propyl-4-methyl-1,3-oxathiane was demonstrated to impart fleshy, seedy, fruity, and enhanced cinnamate notes to the formula.

|  | Parts* | |
|---|---|---|
| Ingredients | + | − |
| Furaneol (Commercially available from Lansdowne Chemical) | 4.00 | 4.00 |
| Ethyl Butyrate (Commercially available from Advanced Biotech) | 2.00 | 2.00 |
| Hexyl butyrate (Commercially available from Global Essence) | 1.00 | 1.00 |
| Cis-3-hexenol (Commercially available from Mitsui & Co., LTD) | 0.80 | 0.80 |
| Gamma-decalactone (Commercially available from Ungerer & Company) | 0.30 | 0.30 |
| Cis-3-hexenyl caproate (Commercially available from Bedoukian Research) | 1.20 | 1.20 |
| Methyl cinnamate (Commercially available from Givaudan Suisse SA) | 3.00 | 3.00 |
| 2-Propyl-4-methyl-1,3-oxathiane, 1% | 0.005 | — |
| Propylene Glycol (Commercially available from IFF) | 87.695 | 87.70 |
| Total | 100.00 | 100.00 |

*"+" represents a 2-propyl-4-methyl-1,3-oxathiane containing formula; and "−" represents a 2-propyl-4-methyl-1,3-oxathiane non-containing formula.

What is claimed is:

1. A compound of Formula I:

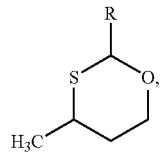

Formula I wherein R is selected from the group consisting of propyl, and 2-(methylthio)ethyl.

2. The compound of claim 1, wherein the compound is 2-propyl-4-methyl-1,3-oxathiane.

3. A process of augmenting, enhancing or imparting taste to a material selected from the group consisting of a foodstuff, a chewing gum, a medicinal product, and toothpaste comprising the step of incorporating an olfactory acceptable amount of a compound of Formula I:

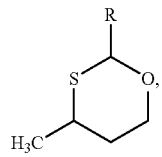

Formula I wherein R is selected from the group consisting of propyl, and 2-(methylthio)ethyl.

4. The process of claim 3, wherein the compound is 2-propyl-4-methyl-1,3-oxathiane.

* * * * *